US00PP17997P3

(12) United States Plant Patent
Abrahamson et al.

(10) Patent No.: US PP17,997 P3
(45) Date of Patent: Sep. 11, 2007

(54) FAST-GROWING WILLOW SHRUB NAMED 'OTISCO'

(50) Latin Name: ***Salix viminalis*×*S. miyabeana***
Varietal Denomination: Otisco

(75) Inventors: Lawrence P. Abrahamson, Marcellus, NY (US); Richard F. Kopp, Marietta, NY (US); Lawrence B. Smart, Geneva, NY (US); Timothy A. Volk, Syracuse, NY (US)

(73) Assignee: The Research Foundation of State University of New York, Albany, NY (US)

( * ) Notice: Subject to any disclaimer, the term of this patent is extended or adjusted under 35 U.S.C. 154(b) by 115 days.

(21) Appl. No.: 11/244,987

(22) Filed: Oct. 6, 2005

(65) Prior Publication Data

US 2007/0083963 P1 Apr. 12, 2007

(51) Int. Cl.
*A01H 5/00* (2006.01)

(52) U.S. Cl. ..... Plt./216
(58) Field of Classification Search ..... Plt./216
See application file for complete search history.

*Primary Examiner*—Kent Bell
(74) *Attorney, Agent, or Firm*—Wall Marjama & Bilinski LLP

(57) ABSTRACT

A distinct female cultivar of *Salix viminalis*×*S. miyabeana* named 'Otisco', characterized by rapid stem growth producing greater than 42% more woody biomass than one of its parents ('SX64') and 33% more biomass than a current production cultivar ('SV1'). 'Otisco' produced greater than 2.5-fold more stem biomass than two other current production cultivars, 'SX67' and 'SX61'. 'Otisco' can be planted from dormant stem cuttings, produces multiple stems after coppice, and the stem biomass can be harvested when the plant is dormant. In the spring following harvest, the plant will re-sprout very vigorously, producing new stems that can be harvested after two to four years of growth. This harvest cycle can be repeated several times. The stem biomass can be chipped and burned as a source of renewable energy, generating heat and/or electricity. 'Otisco' displays a low incidence of rust disease and is not damaged by potato leafhoppers.

10 Drawing Sheets

STATEMENT AS TO RIGHTS TO INVENTIONS MADE UNDER FEDERALLY-SPONSORED RESEARCH AND DEVELOPMENT

The invention described herein was reduced to practice during the funding period of Contract 4000003235 (SUNY Research Foundation Award 011275) awarded by Oak Ridge National Laboratory, managed by UT-Batelle for the United States Department of Energy under contract DE-AC05-00OR22725, and of agreement number 6267 (SUNY Research Foundation Award 011536) awarded by the New York State Energy Research and Development Authority.

CROSS-REFERENCE TO RELATED APPLICATIONS

This application is related to the following plant patent applications, all of which are subject to assignment to the Research Foundation of the State University of New York, and each of which is being filed on even date herewith: "Fast-Growing Shrub Willow" Named 'Fish Creek', application Ser. No. 11/244,988, "Fast-Growing Shrub Willow" Named 'Canastota', application Ser. No. 11/244,986, "Fast-Growing Shrub Willow" Named 'Millbrook', application Ser. No. 11/244,636, "Fast-Growing Shrub Willow" Named 'Oneida', application Ser. No. 11/244,975, "Fast-Growing Shrub Willow" Named 'Owasco', application Ser. No. 11/244,842, and "Fast-Growing Shrub Willow" Named 'Tully Champion', application Ser. No. 11/244,635, The variety of fast-growing shrub willow named 'Otisco' was produced in the willow breeding program at the State University of New York College of Environmental Science and Forestry, as were other varieties, including: 'Fish Creek', 'Canastota', 'Millbrook', 'Oneida', 'Owasco', and 'Tully Champion'.

BACKGROUND OF THE INVENTION

1. Field of the Invention

The invention is a new and distinct cultivar known by the varietal name 'Otisco' resulting from the novel hybridization of *Salix viminalis* with *Salix miyabeana*. The new variety was produced through controlled willow breeding conducted by the inventors at the State University of New York College of Environmental Science and Forestry in Syracuse, N.Y. The objective of the breeding program is to produce new willow cultivars that generate high biomass yields on a variety of sites, are resistant to diseases and pests, and possess agronomic traits suitable for mechanical planting, harvesting, and post-harvest processing. Shrub willow is being developed as an agricultural crop plant that will be grown and harvested as a sustainable, renewable source of energy. Once a field planting of shrub willows is established, the woody stems can be harvested every three years, and new shoots will re-sprout the following season. Repeated harvesting every two to four years can be sustained for at least 15 years.

2. Description of Relevant Prior Art Including Information Disclosed Under 37 CFR 1.97–1.99

This new variety of *Salix viminalis*×*Salix miyabeana* was the seedling progeny of the controlled pollination of the female clone *S. viminalis* 'SV2' by the male clone *S. miyabeana* 'SX64' performed in February 1999 in Syracuse, N.Y. The plant has been propagated repeatedly by stem cuttings and has been found to retain its distinctive characteristics through successive propagations and field trials. More specifically, the plant has been asexually reproduced by collecting dormant stems during the winter months from a plant growing in Syracuse, N.Y.; cutting them into either 5" to 10" pieces (cuttings); then planting those cuttings in the field in Tully, N.Y. in the spring or in potting mix in the greenhouse, then transplanting the rooted cuttings to the field in Tully, N.Y. Both parents were originally transferred from Toronto, Ontario, Canada to Syracuse, N.Y. and were vegetatively propagated from stem cuttings. The female parent (*S. viminalis* 'SV2') was transferred in 1990, while the male parent (*Salix miyabeana* 'SX64') was transferred in 1994. The female parent (*Salix viminalis* 'SV2') has leaves that are narrowly lanceolate and with acute apex. They are pubescent underneath with raised veins and margins are entire. Mature leaves of variety 'Otisco' are lanceolate with acuminate apex, upper and lower surfaces are glabrous and margins are serrulate. The growth of the parent plants was characterized in nursery plantings in Tully, N.Y. The male clone *Salix miyabeana* 'SX64' displayed rapid stem growth and low incidence of rust disease, so was chosen to serve as a parent in a cross with *S. viminalis* 'SV2', which suffered from susceptibilty to the potato leafhopper (*Empoasca fabae*). The seedlings produced by this cross (identification #99201) were first established in a greenhouse, and then were transplanted to Syracuse, N.Y. This particular individual (identification #99201-007) was selected from the family due to its exceptional stem height growth.

The new cultivar has been grown in Syracuse, N.Y. and Tully, N.Y., which have a normal yearly average daily temperature of 47° F., normal daily maximum temperature in July of 82° F., normal daily minimum temperature in January of 14° F., and average precipitation of 40 inches. The new cultivar grows from a rooted cutting to a fully mature plant ready for harvest in approximately three years.

SUMMARY OF THE INVENTION

The *Salix viminalis*×*S. miyabeana* cultivar 'Otisco' has not been observed under all possible environmental conditions. The phenotype may vary somewhat with variations in environments such as temperature, light intensity and length of illumination, without, however, any variation in genotype. The new and distinct cultivar presents the following traits that have been repeatedly observed and are determined to be the unique characteristics of 'Otisco'. These characteristics in combination distinguish 'Otisco' as a new and distinct cultivar:

1. Rapid growth rate, producing greater than 42% more woody biomass than one of its parents (*Salix miyabeana* 'SX64'), 33% more biomass than one current production cultivar (*Salix dasyclados,* 'SV1'), and more than 2.5-fold more biomass that two other production cultivars (*Salix miyabeana* 'SX67' and *Salix sachalinensis* 'SX61') when grown in the same field for the same length of time (two growing seasons after coppice) in Tully, N.Y.
2. Resistance to potato leafhopper, which causes severe stunting of growth, curling of the leaves, and overall decline in vigor (all characteristic of hopper burn) on the female parent, *S. viminalis* 'SV2'.
3. Low incidence of rust disease assessed in experimental trials in Syracuse, N.Y. in 2000.

BRIEF DESCRIPTION OF THE DRAWING

The accompanying color photographs show the features of the claimed cultivar in a manner as true as is reasonably possible. The illustrations include:

FIG. 1.1 illustrates two-year-old portion of stem collected while dormant;

FIG. 1.2 illustrates one-year-old portion of stem collected while dormant;

FIG. 1.3 illustrates a vegetative bud in dormancy;

FIG. 1.4 illustrates a floral bud in dormancy;

FIG. 1.5 illustrates new shoot growth from a stem cutting rooted in soil:sand in a greenhouse;

FIG. 1.6 illustrates upper leaf surface;

FIG. 1.7 illustrates lower leaf surface;

FIG. 1.8 illustrates mature catkin;

FIG. 1.9 illustrates pistil and densely pubescent floral bract; and

FIG. 2.1 illustrates biomass yield two years after coppice for the claimed cultivar as compared to other shrub willows.

DETAILED DESCRIPTION OF THE NEW PLANT

The following detailed description sets forth characteristics of the new plant. The following observations and measurements describe plants grown by asexual reproduction in Syracuse, N.Y. or Tully, N.Y. under conditions as described hereinabove. Color references are made using The Royal Horticultural Society Colour Chart (hereinafter The R.H.S. Colour Chart) of The Royal Horticultural Society of London, England, except where general terms of ordinary dictionary significance are used.

BOTANICAL DESCRIPTION OF THE PLANT

The following detailed description of the 'Otisco' variety is based on observations from 10 inch cuttings grown in a greenhouse in Syracuse, N.Y. Cuttings were grown in 7 inch tubes in a (1:1) ProMix®/sand (v/v) substrate under natural light from December 2004 to March 2005. Plants were irrigated with automatic misting for 6 minutes every 2 hours five times each day.

Latin name: *Salix viminalis*×*S. miyabeana.*
Varietal denomination: 'Otisco'.
Parentage:
*Female or seed parent.*—*S. viminalis* 'SV2'.
*Male or pollen parent.*—*S. miyabeana* 'SX64'.
Propagation:
*Type.*—Stem cutting.
*Time to rooting.*—Approximately 10 days in water at 21° C.
Precocity: Subprecocious — Catkins mature as leaves begin to break bud.
Plant description: The color of one-year-old stem cuttings observed when dormant are grey orange (RHS 167B), while two to three-year-old stems are yellow-green (RHS 153B) to cracking pale green (RHS 195B) bark. Vegetative buds are red-orange (RHS 179A), obtuse, linear, pubescent, and typically 3.5–4 mm in length. Lenticels are red, large, wart-like, and numerous. The leaves are simple and alternate with pinnate venation. The upper surface of field-grown leaves in early October is glabrous and glossy with distinct pinnate venation. The lower surface is glabrous and slightly glaucous. Stipules are lanceolate, serrulate, slightly curved, and typically 4 mm in length. Immature leaves are pubescent. Mature leaves are lanceolate, acuminate apex, acute base, typically 8.5–9.6 cm in length, 1.1–1.8 cm in width, serrulate margin, adaxial (upper) surface green (RHS 144A), abaxial (lower) surface pale green (RHS 143D), and stem light pale green (RHS 145B) at 6 weeks of growth. Typical petioles on mature leaves grown under field conditions in early October are yellow-green (#N144D) and are 1.0–2.0 mm in diameter. The petiole depicted FIGS. 1.6 and 1.7 from a greenhouse-grow plant is green (#138D) and 1 mm in diameter. The typical diameter of two-year old stems at a height of 1 m is 1.3 cm. The bark color of field-grown stems determined in early October after two growing seasons is greyed-green (#194B). The surface is textured with thin longitudinal furrows and raised reddish lenticels. The average plant height of a mature plant after three seasons of growth is 5–6 m with a typical spread at the crown of 1.0–1.5 m when grown in the typical planting spacing of 0.6 m×0.7 m.

Flowering description: Dormant floral buds are elongated, ovoid, acute, typically 9 mm in length, appressed, and red-orange (RHS 171A). Peduncle of catkin is typically 3.5 mm in length and bears 4 leafy bracts. Catkins are erect, typically 2.8 cm in length, narrowly cylindrical, and densely flowered. Flowers have a long, narrow, densely hairy, and sessile ovary, with a long style and 2 stigmas one larger than the other. Floral bract is densely pubescent and has a pink acute apex.

Field growth characteristics: Determined through surveys of plants growing at the LaFayette Road Experiment Station in Syracuse, N.Y.

Disease resistance: Displays a low incidence of rust disease.

Temperature tolerance: Stems typically do not suffer frost damage at temperatures as low as 10° F. and may suffer only minor tip dieback at lower temperatures.

Seed production: 'Otisco' produces only female flowers, so viable seeds will only be produced after pollination by a compatible male variety. This has not yet been observed in field trials.

Biomass yield: Mean dry stem biomass yield produced through two growing seasons after coppice in each of eight four-plant plots ('Otisco', 14.78 oven dry tons $ha^{-1}$ $yr^{-1}$) measured in a yield trial growing at the Tully Genetics Field Station in Tully, N.Y. in February 2005 was 42% greater than the mean stem biomass yield of one of its parents ('SX64', 10.35 oven dry tons $ha^{-1}$ $yr^{-1}$) and was 33% greater than a current production cultivar ('SV1', 11.04 oven dry tons $ha^{-1}$ $yr^{-1}$) growing in the same trial (FIG. 2.1). 'Otisco' produced greater than 2.5-fold more stem biomass than two other current production cultivars ('SX67', 5.52 oven dry tons $ha^{-1}$ $yr^{-1}$; 'SX61', 4.83 oven dry tons $ha^{-1}$ $yr^{-1}$) growing in the same trial (FIG. 2.1).

What is claimed is:

1. A new and distinct variety of a *Salix viminalis*×*S. miyabeana* plant substantially as illustrated and described herein.

* * * * *

Fig. 1.1
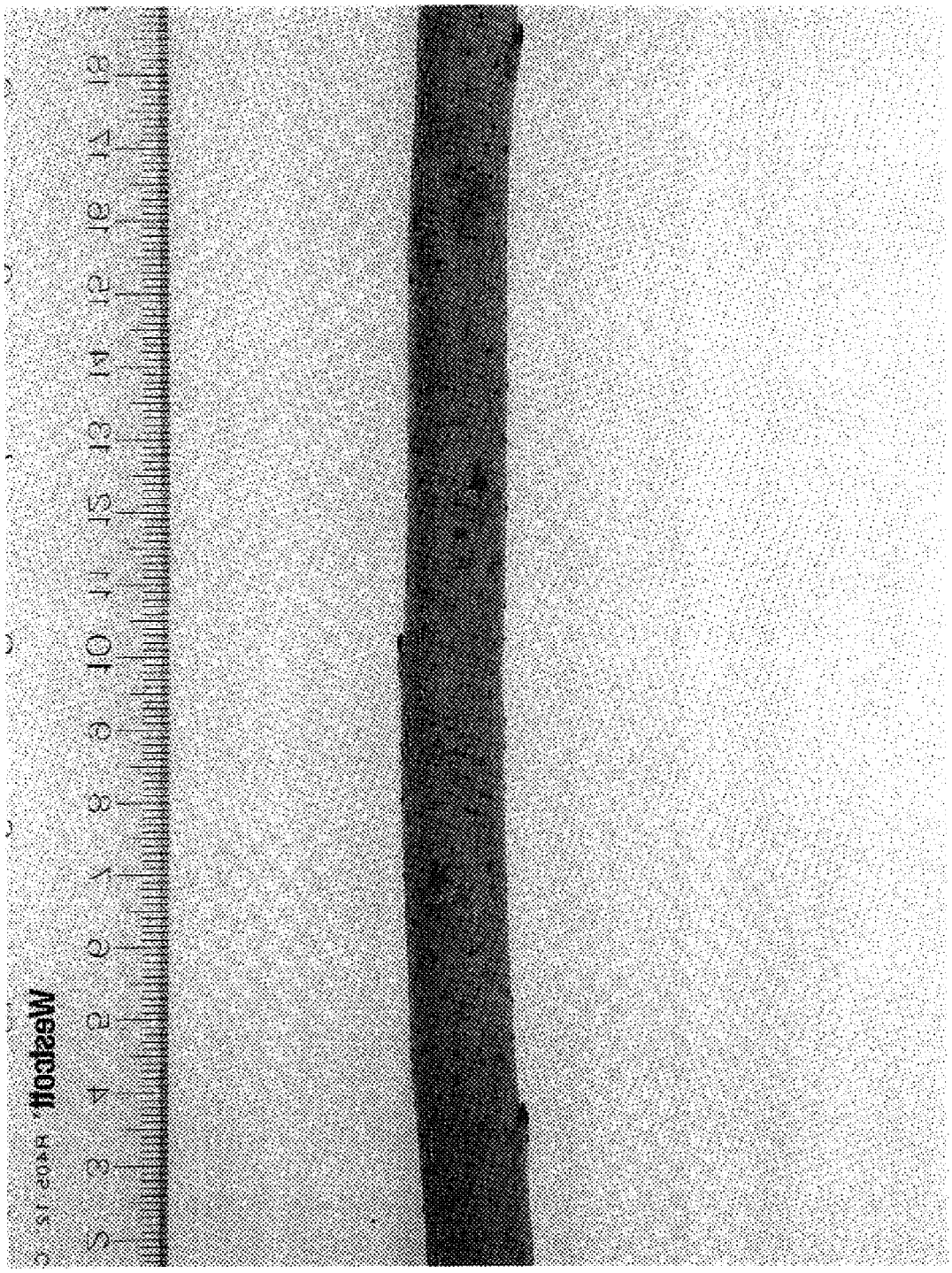

Fig. 1.2
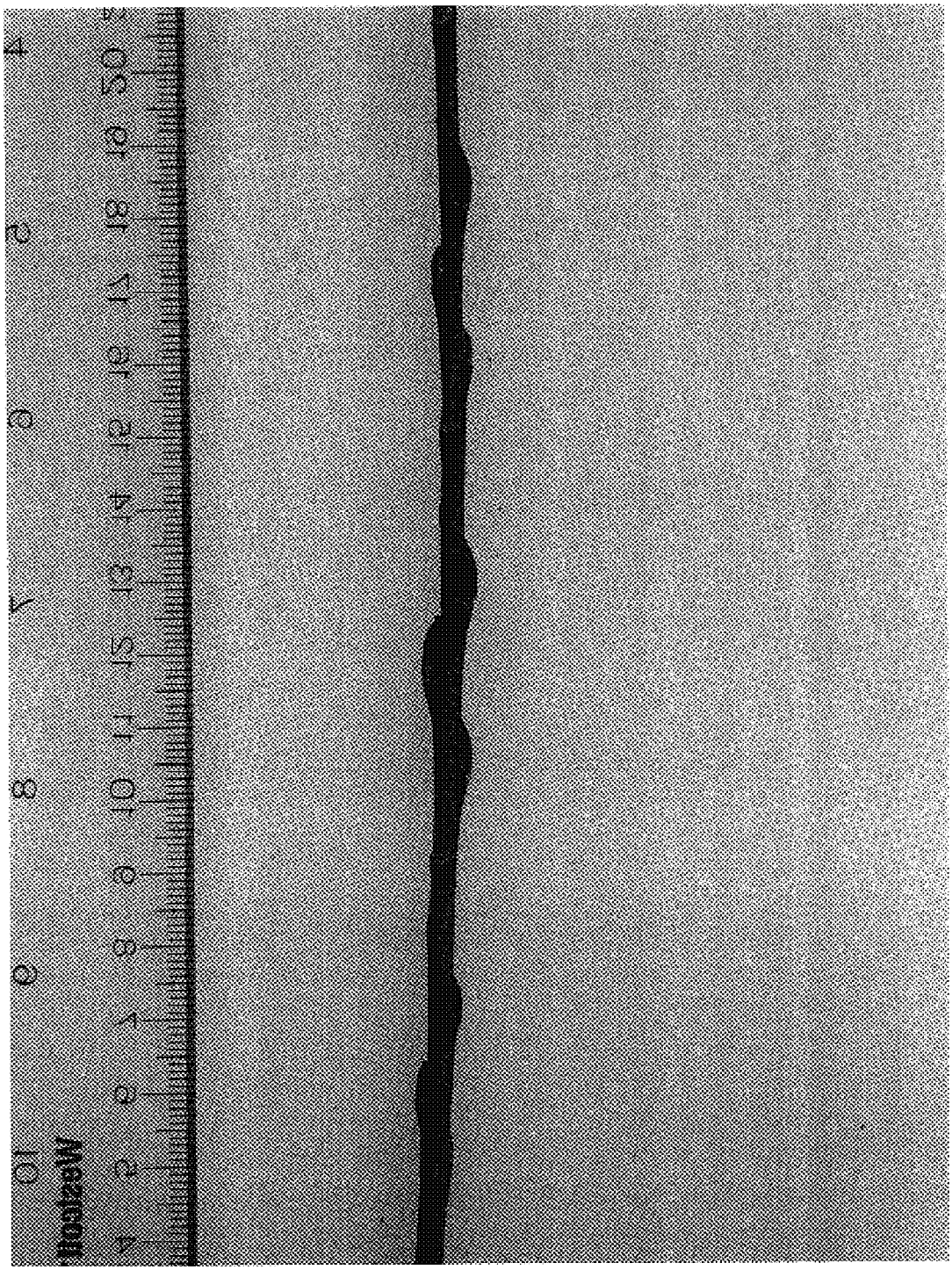

Fig. 1.3
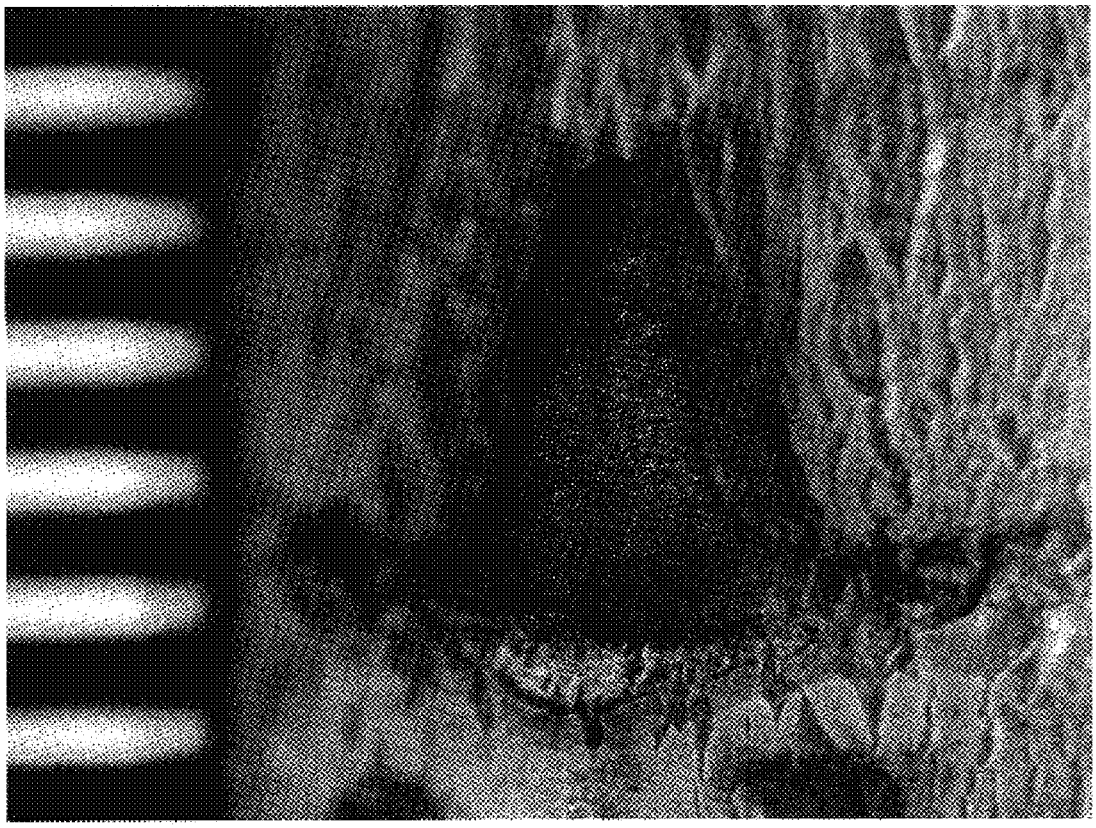

Fig. 1.4
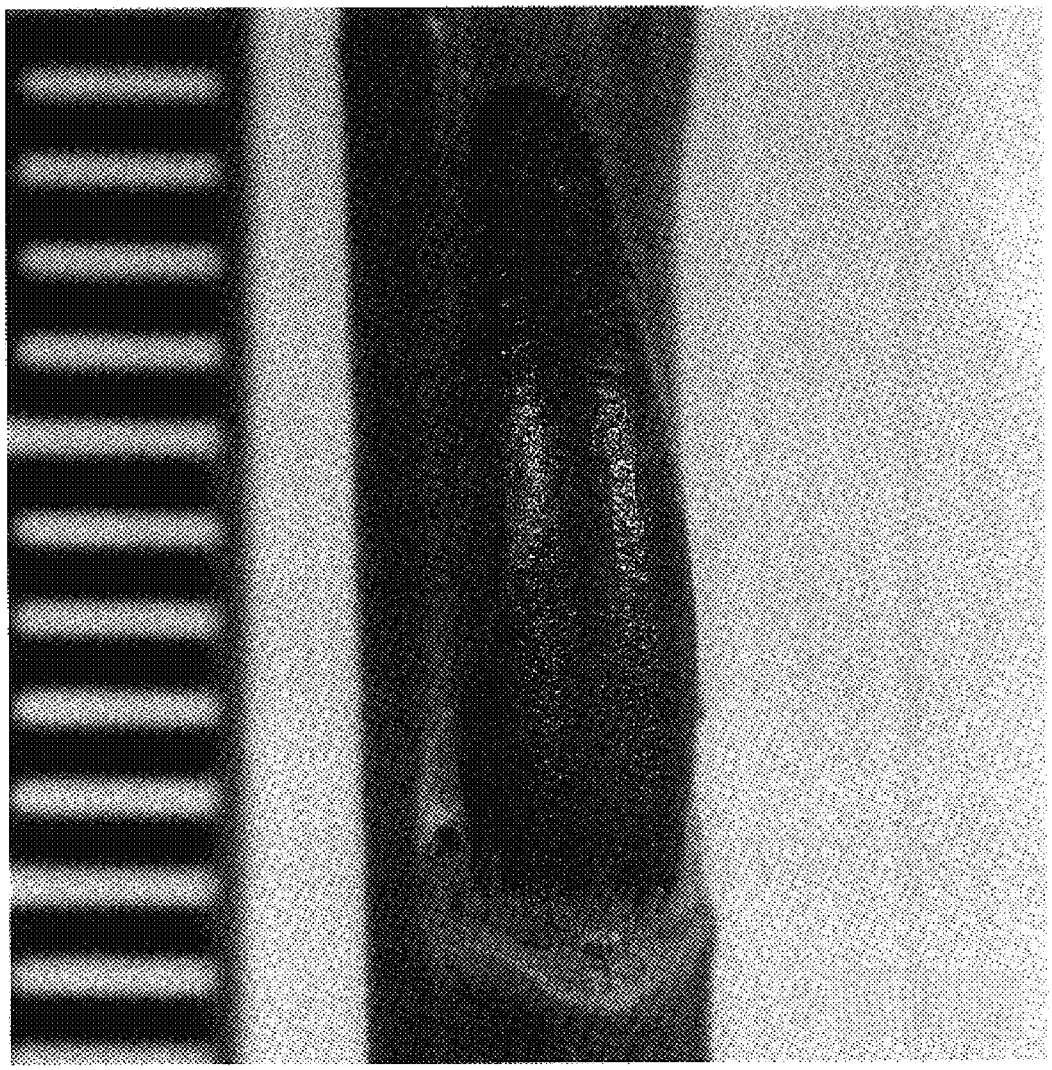

Fig. 1.5
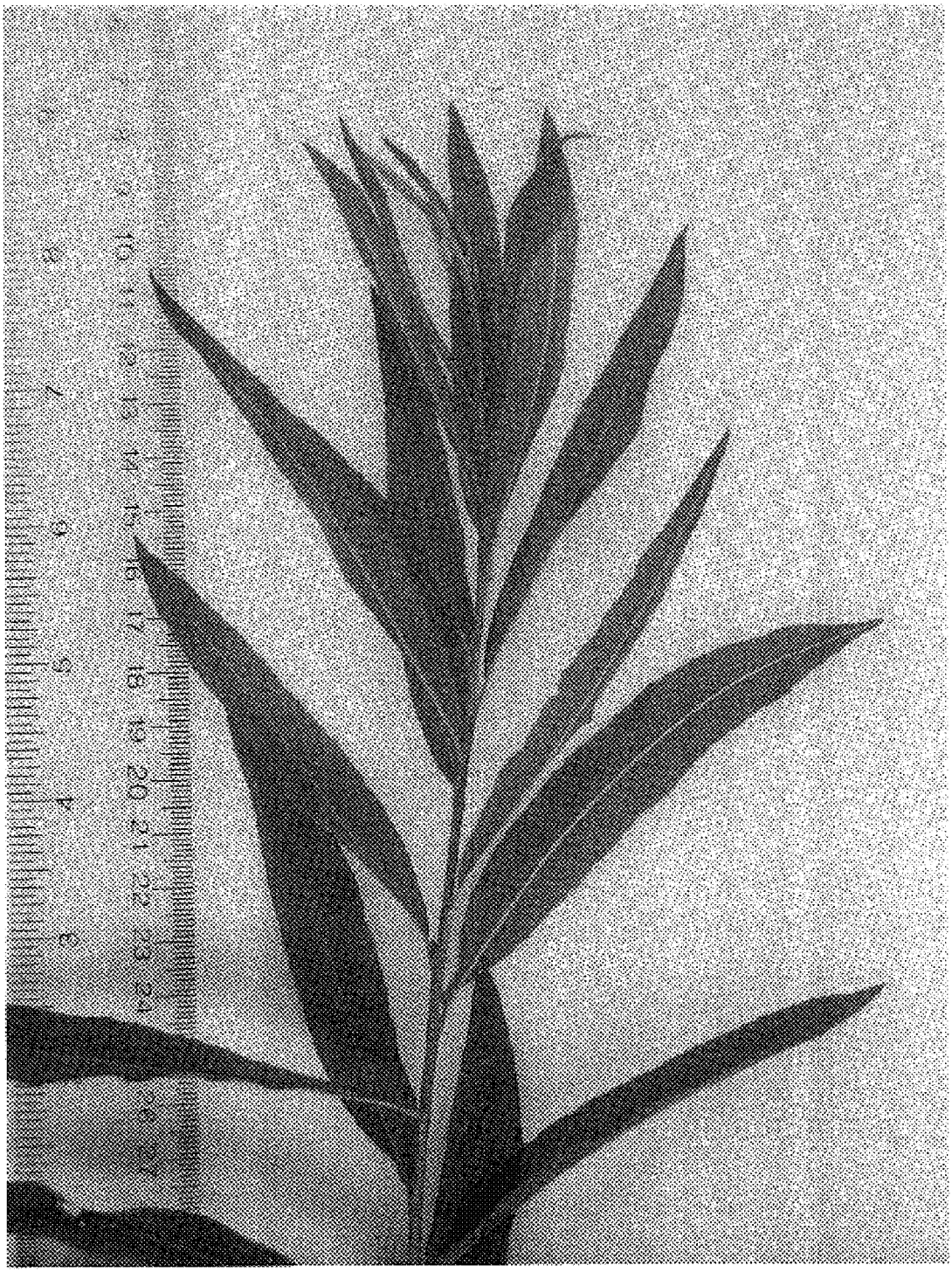

Fig. 1.6
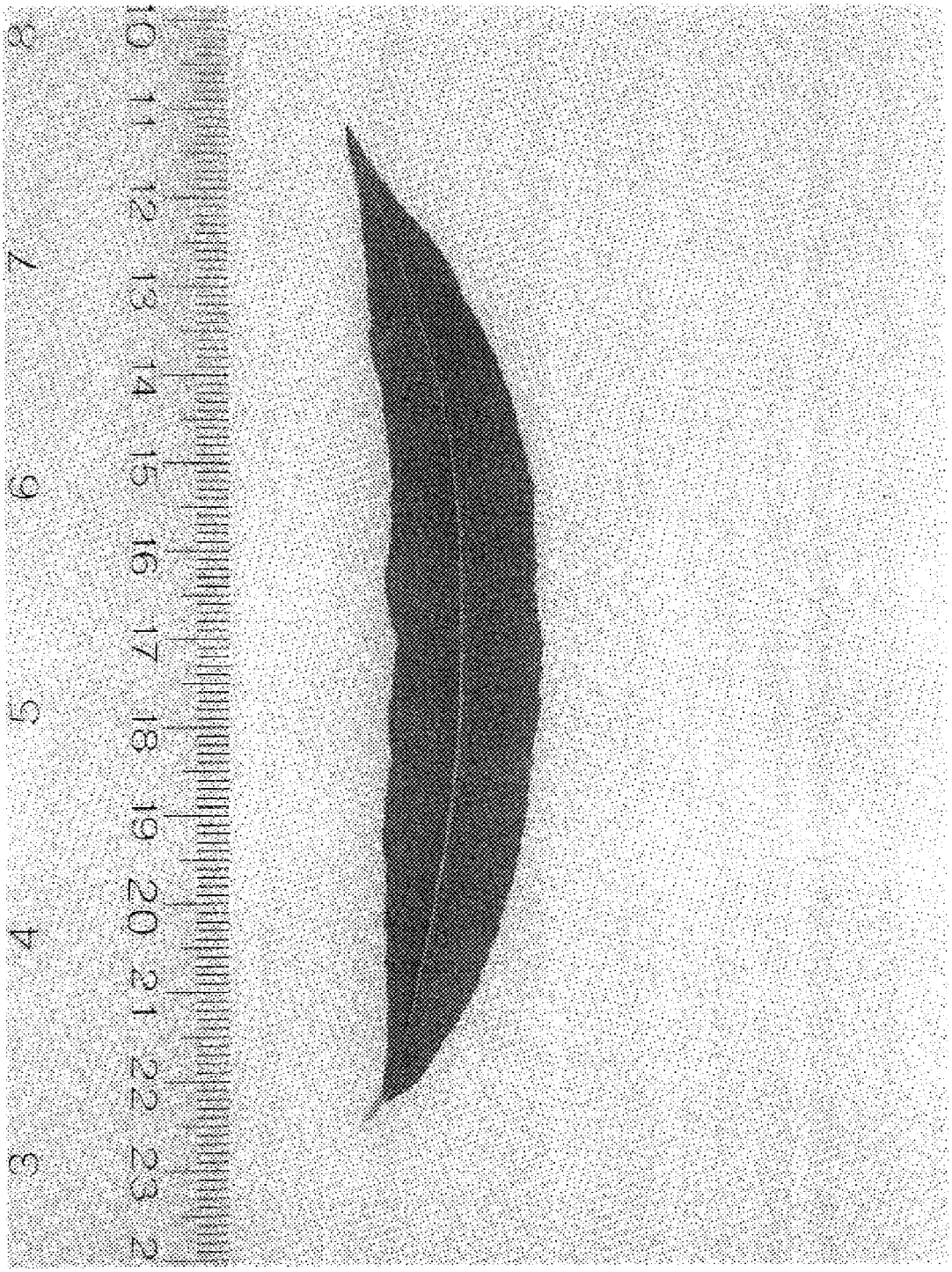

Fig. 1.7
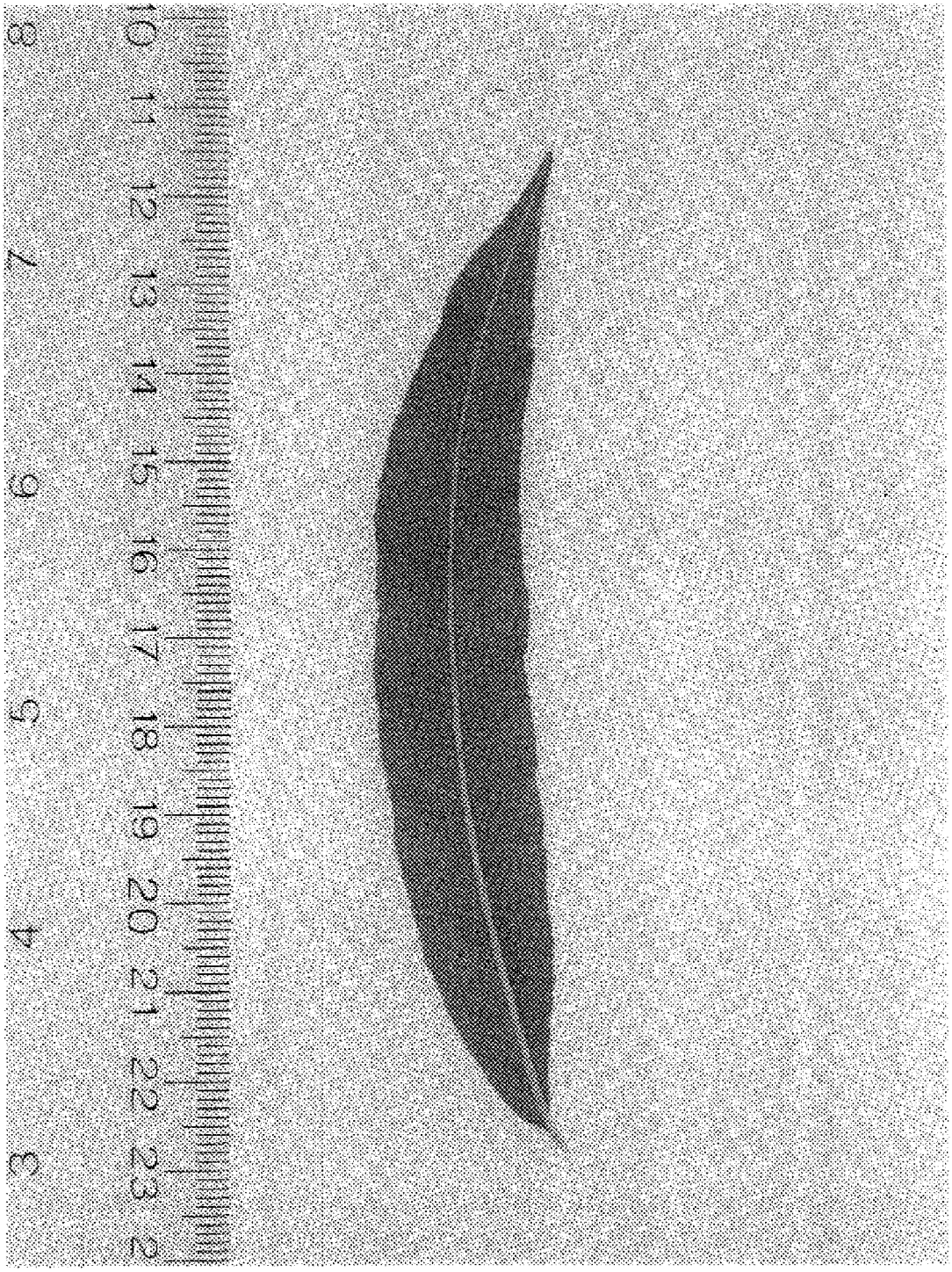

Fig. 1.8
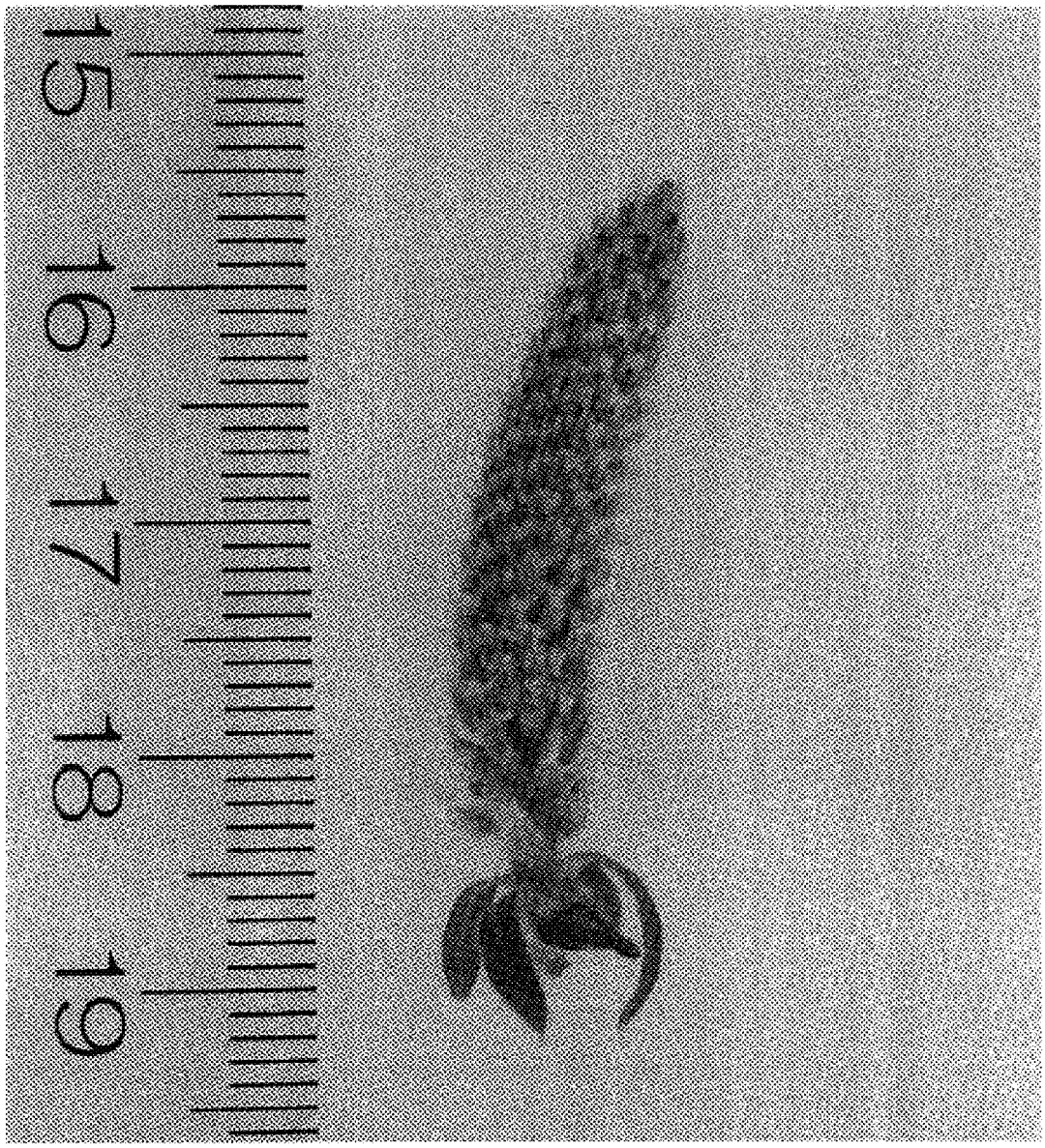

Fig. 1.9
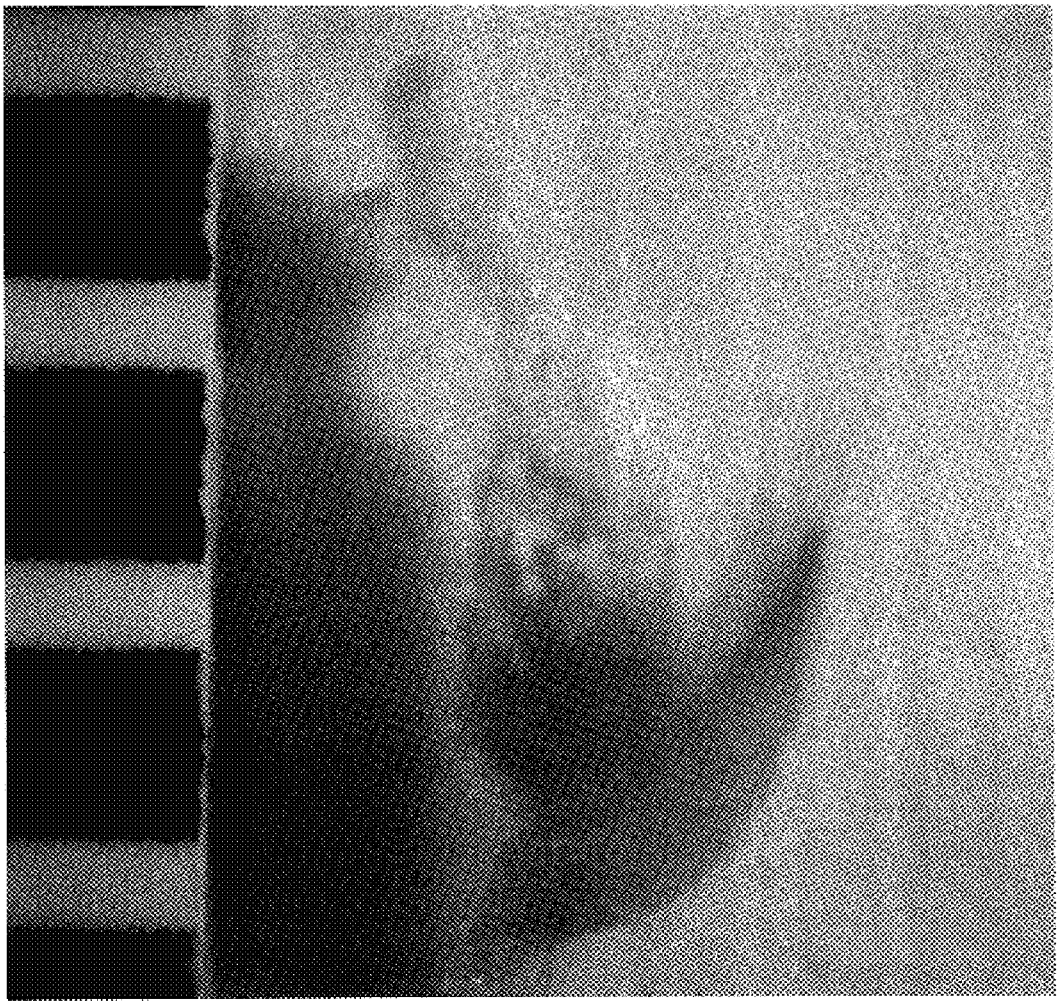

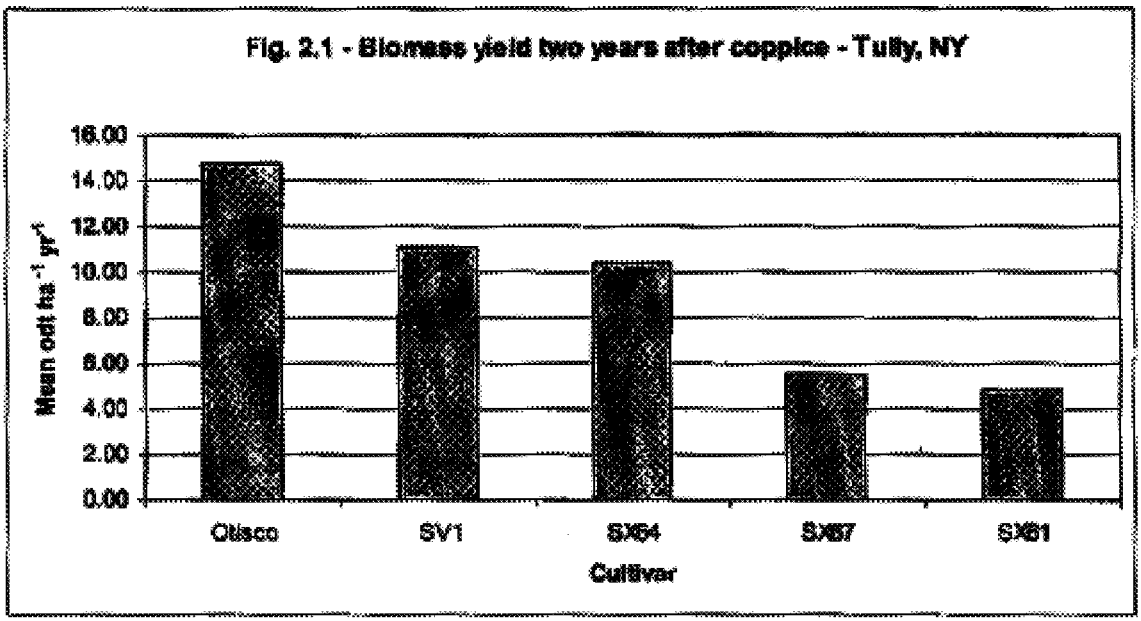
Fig. 2.1 - Biomass yield two years after coppice - Tully, NY
16.00
14.00
12.00
10.00
8.00
6.00
4.00
2.00
0.00
Mean odt ha-1 yr-1
Otisco
SV1
SX64
SX67
SX61
Cultivar